Figure 1:
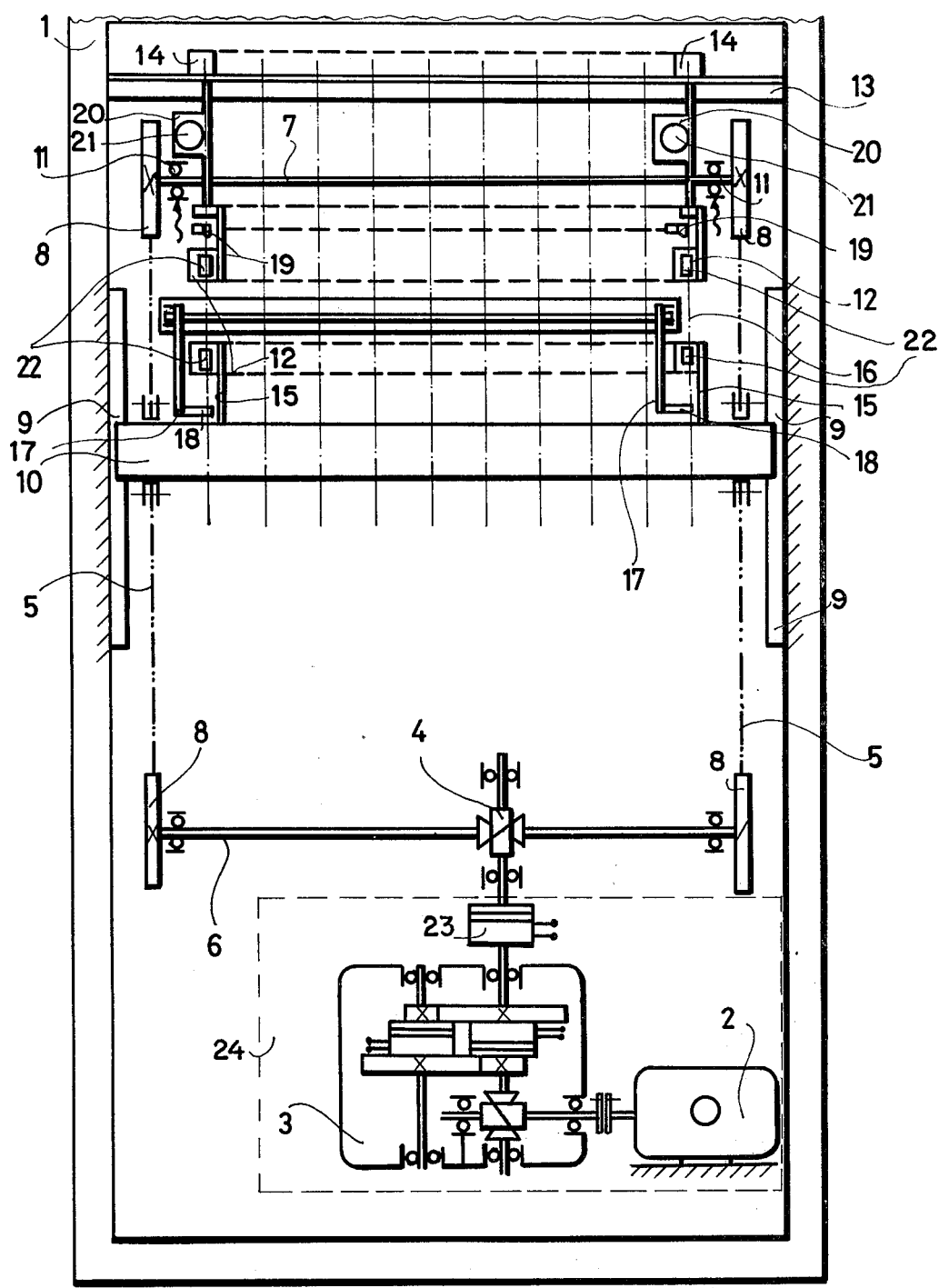

United States Patent [19]

Katona et al.

[11] 4,173,787

[45] Nov. 6, 1979

[54] EQUIPMENT FOR THE AUTOMATIC, SUPER-SPEED, AND LARGE-SCALE YARN-STRENGTH TESTING

[75] Inventors: Tibor Katona; Tamás Kenderesy; Imre Nemes; Agoston Erdélyi; József Ragályi, all of Budapest, Hungary

[73] Assignee: Textilipari Kutato Intezet, Budapest, Hungary

[21] Appl. No.: 842,329

[22] Filed: Oct. 11, 1977

[30] Foreign Application Priority Data

Oct. 12, 1976 [HU] Hungary .................. TE 860

[51] Int. Cl.² .................. G01N 3/00; G06F 15/46
[52] U.S. Cl. .................. 364/550; 73/828; 73/160; 325/38 B; 364/506
[58] Field of Search ............ 364/506, 507, 550, 551; 73/160, 95.5; 325/38 B; 332/11 D

[56] References Cited

U.S. PATENT DOCUMENTS

| | | | |
|---|---|---|---|
| 3,499,321 | 3/1970 | Baker | 73/95.5 |
| 3,533,284 | 10/1970 | Slemmons et al. | 73/160 |
| 3,710,056 | 1/1973 | Tomozawa | 325/38 B |
| 3,835,385 | 9/1974 | Hoeschele, Jr. et al. | 325/38 B |
| 3,878,465 | 4/1975 | Stehenne et al. | 325/38 B |
| 3,971,987 | 7/1976 | Carrubba et al. | 325/38 B |

OTHER PUBLICATIONS

Dorrity et al.; A Minicomputer-Controlled All-Digital Tensile Test System, Proceedings IEEE., vol. 63, No. 10, Oct. 1975, pp. 1451-1459.
Instron Ltd.; Garuprüf Apparat Model 1150 (Trade Publication-British).
Zwick GmbH: Zugprüfmaschine 1510 (Trade Publication-West German).

Primary Examiner—Felix D. Gruber
Attorney, Agent, or Firm—Young & Thompson

[57] ABSTRACT

The invention is related to a composite material testing equipment designed for the automatic, super-speed, and large-scale yarn-strength testing in a manner affording the possibility of displaying and recording the results of the said tests continuously and — practically — at the same time as the test takes place.

N pieces of breaking units each of them comprising at least one sensor are mounted upon a common supporting block, and coupled to a single, common drive. The program-controlled drive and the sensors are connected to the control unit of a data processing and control network. The network comprises a RAM-memory connected to several channels of the control unit whereas its data outputs are parallelly connected to the inputs of two registers, the outputs of the registers being coupled to an adder stage, and the output of the latter is connected to a D/A converter. The outputs of the second register are also connected to the data inputs of the RAM-memory, the output of the D/A converter is connected to one input of a set of comparators, the other inputs of the comparators are connected to one of the said sensors each, and the outputs of the comparators are connected to the inputs of channel selector which is coupled with the control unit, and the output of the channel selector is also connected to the respective input of the second register.

8 Claims, 6 Drawing Figures

EQUIPMENT FOR THE AUTOMATIC, SUPER-SPEED, AND LARGE-SCALE YARN-STRENGTH TESTING

The invention is related to a composite material testing equipment designed for the automatic, super-speed, and large-scale yarn-strenth testing in a manner affording the possibility of displaying and recording the results of the said tests continuously and—practically—at the same time as the test takes place.

In the textile industry, especially in the spinning, there is a constant need of testing the quality of the "continuous" filament yarn, on a large scale and continuously. Initially, mechanical tensile-testing machines were used for this purpose. In the course of time, a multiple of such machines was simultaneously used in order to accelerate the work. Efforts were made to perform the material testing in the course of and simultaneously with the manufacture in order to find out any yarn defect before the defective charge would be processed. For this purpose, the tensile-testing machines underwent automation, and the quality parameters were recorded as line diagrams or displayed by counting devices.

However, even the most up-to-date, and more or less automatized material testing methods could not keep pace with the development of the manufacturing process so that the rate of the material testing falls always behind that of manufacturing. The evaluation of the test results is therefore usually only established when the processing of the yarn charge in question is already completed. Owing to this slowness of the product qualification, there is still no way to interfere in the manufacturing process in time, no possibility to make an early change in some of the technological features in order to "adjust" the required quality features during a run. The modernization as mentioned hereinbefore went on in two directions viz. on the one hand the testing devices were multiplied and, on the other hand, an automation of the operations took place; however, the said two directions are governed by contradictory conditions. The automation can only guarantee the necessary supervision of quality if means of a very high pricision and reliability are applied since the human interference is more and more diminished, the human supervision can thus not immediately reveal the defective operations, and the avoidance of such becomes more and more the task of the machinery itself. The modernization by way of automation is therefore carrying enormous costs and requiring very large investment even if only a one-channel measurement is concerned. On the other hand, if the design of a multiple machine is desired comprising more or many simultaneous channels, the multiplication of the costly high-performance elements mentioned above would be unbearable.

There are two processes where the said problem is especially to be faced.

A stability problem arises with the sensors of the force transducers because of the signal errors owing to the drift, errors to be eliminated separately at each channel. As force transducers, inductive sensors are generally used which are very costly, and the necessity of using a carrier-frequency amplifier of special construction makes the system still much more expensive.

The evaluation of the results of the parallel multi-channel measurement is also very expensive. One way is its performance using an on-line calculator. The breaking of the different samples takes place almost at the same time. A multiplex A/D converter is adapted to convert such results simultaneously only if it is of a special construction and very expensive, and even in this case is it very difficult to make a 12 bit variant of such. If, on the contrary, the multiple use of a set of traditional one-channel converters of 12 bit capacity is chosen, the horrible increase of the costs seems to be even more evident.

The invention is based on the concept that the optimum solution could up till now not be found because in the course of the developing activity:

either the increase of the quality and working speed of the up-to-date components used in the equipment required abandoning the multiple embodiment, or the multiplication required abandoning a high precision and reliability of the testing, and no evaluation was made as far as the performance of the multiplied measuring systems is concerned whereas the complete elimination of the measuring errors thus arising can be obtained in the course of the subsequent multi-channel processing of the measuring data by making a better and many-sided use of some means being applied so that only a relatively small increase of expenses is to be reckoned with.

This way is so much the more expedient since the specific costs of any increase in the precision of both the mechanical devices and the precision mechanical components used in the mechanical-electronic transducers are much greater than those necessary to inprove the precision of the electronic data processing.

If there are ten traditional—high-precision and therefore high-priced—force transducers arranged side by side, the expenses would be unbearable considering the present manufacturing conditions. According to the invention, simple sensors are used as far as the drift effect is concerned avoiding the problem of zero-compensation in the carrier frequency amplifier and its RC-network/amplitude, phase/. The drift of the simple dc amplifiers can in a highly precise and reliable manner be compensated by way of automatic digital means.

The conversion of the sample breaking data is performed at different levels by a method that can be considered a virtually simultaneous conversion. In consists essentially in that the instant measuring data supplied by the different sensors are coupled to the A/D converter over a high-speed digital multiplexer and—after conversion—entered into a RAM-memory where they are memorized until the data of the subsequent sampling are obtained. If the measured value of the subsequent sampling period is different from the previous one the A/D converter has only to convert the difference between the value measured subsequently and the one stored in the memory. Considering the sampling rate, the A/D converter as used in an embodiment reduced to practice was only burdened with the task to convert 1 bit/5 ms, a task that can be performed by means of a very simple construction. The said method is that much the less expensive since a RAM-memory is anyway needed for the multi-channel data processing because the system performing the data processing such as a computer cannot avoid the back-play of the data at the end of each cycle so that this way is an economic variant using the RAM-memory—beside its initial purpose—also as a component of the conversion system.

The invention is related to an equipment for the automatic, super-speed, and large-scale yarn-strength testing comprising a control unit for the concerted control of both the breaking process and the processing of the measured data, means for supplying electric signals proportional to the values of the breaking force and the elongation, the said means being connected to one or more data processing unit/s/ whereas the latter one/s/ is /are/ connected to a display and/or printing device, and the data processing unit/s/ and the control unit are expediently coupled onto a computer.

The improvement consists in that n pieces /n is a positive integer/ of breaking units each of them comprising at least one sensor, are mounted upon a common supporting block and coupled to a single, common, program-controlled drive the control input of which is connected to one output of the said control unit, and a data processing and control network is incorporated into the equipment comprising a RAM-memory which is coupled over an address channel, a read-in control channel, and a readout control channel to the said control unit, and over its data output to the inputs of a first and a second register, the outputs of the said registers are coupled to the inputs of an adder stage and the output of the second register is also connected to the data input of the said RAM-memory, the output of the said adder stage is connected to a D/A converter and the output of the D/A converter is connected to a set of comparators over one of their data inputs whereas the other data inputs of the said comparators are separately connected to one of the said sensors each, and the outputs of the said comparators are connected to the input of channel selector, which is coupled with the said control unit and the output of which is coupled to one of the inputs of the second register.

The invention will now be described more particularly with reference to the accompanying drawings.

FIG. 1 is a sketch showing the operational mechanism of a tensile-strength testing machine equipped with ten simultaneously working measuring units.

Figure 2A:
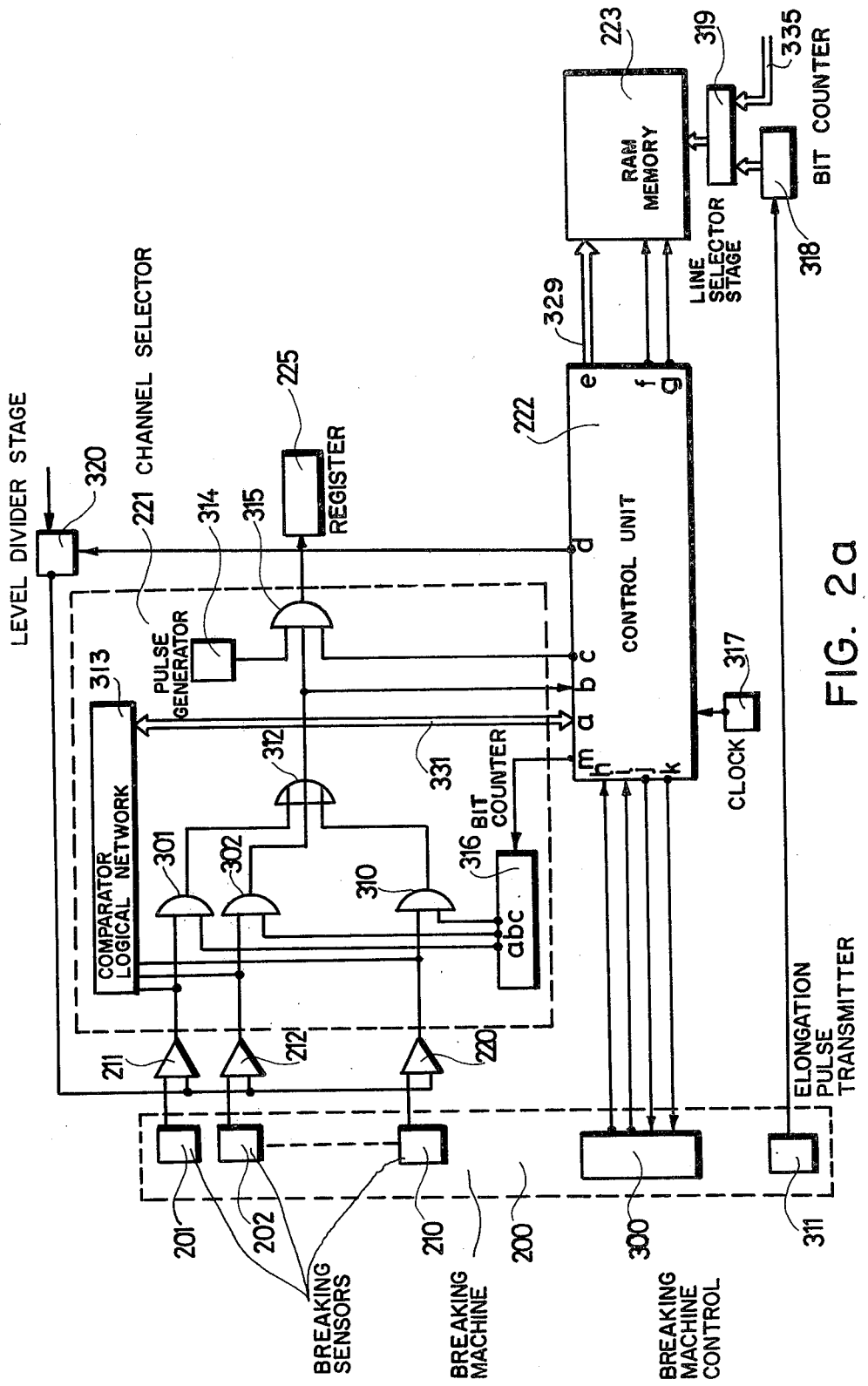
Figure 2B:
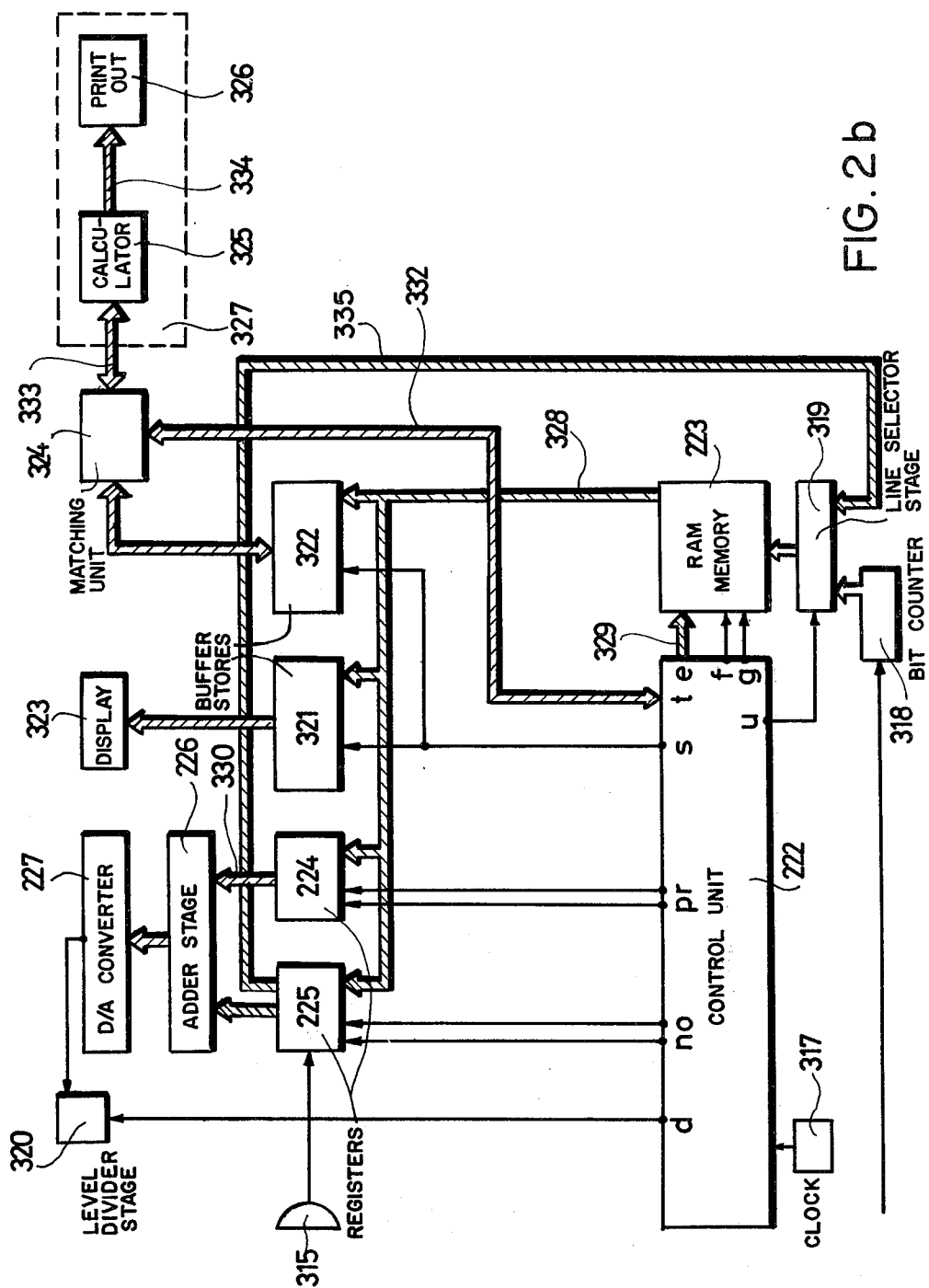

FIG. 2 shows the block diagram of a real embodiment of the data processing and control network; some parts of it are shown at the level of a block diagram whereas other ones with the particulars of a wiring diagram if necessary for easy understanding. In order to make it easy to survey, FIG. 2 is made in two parts, FIG. 2a and FIG. 2b, and at the cutting plane of the two sections some units are shown in both of them in order to facilitate the reading together of the two separate sections.

Figure 3:
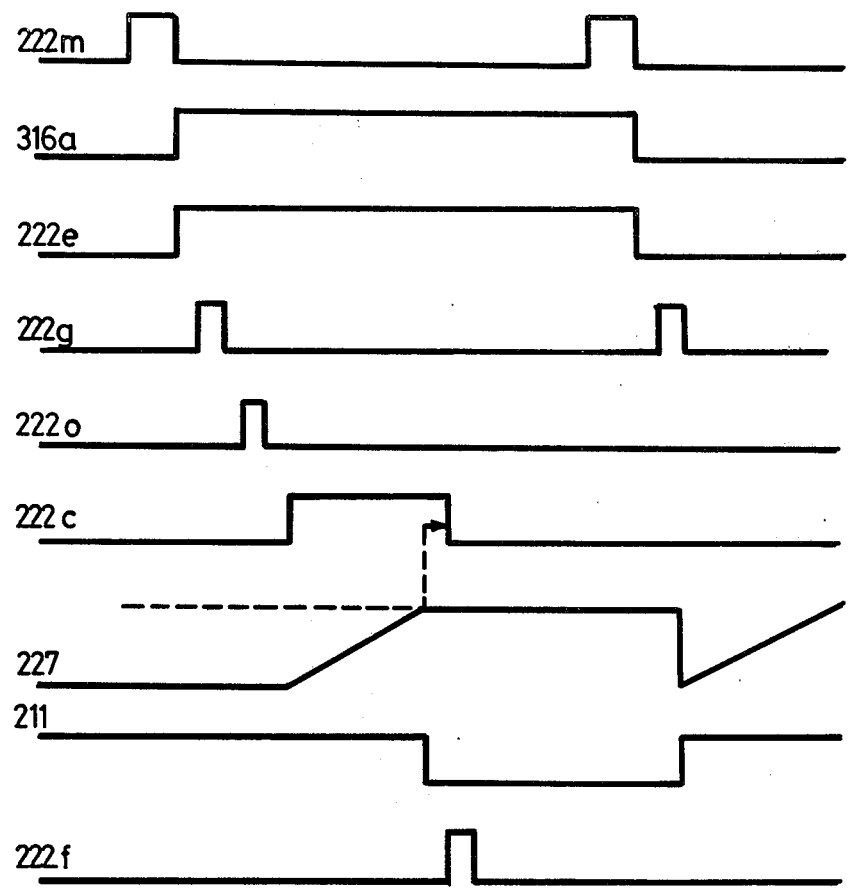
Figure 4:
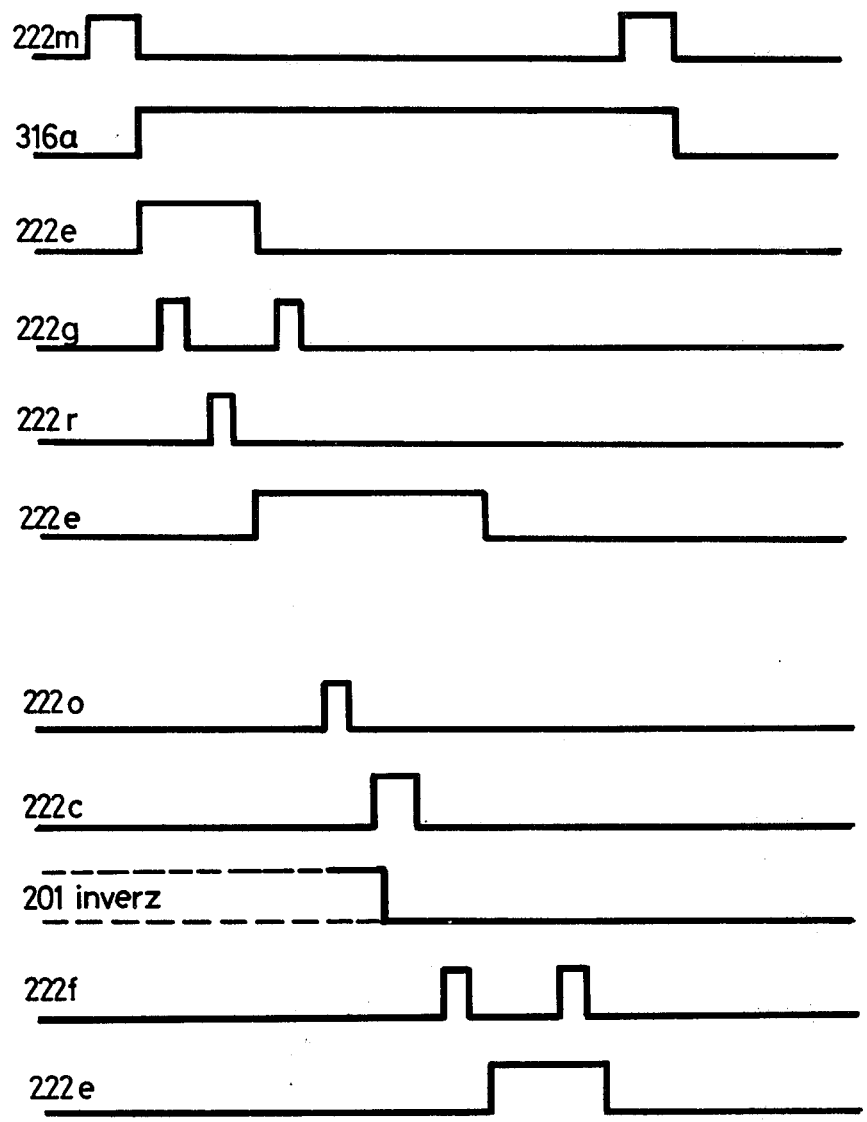
Figure 5:
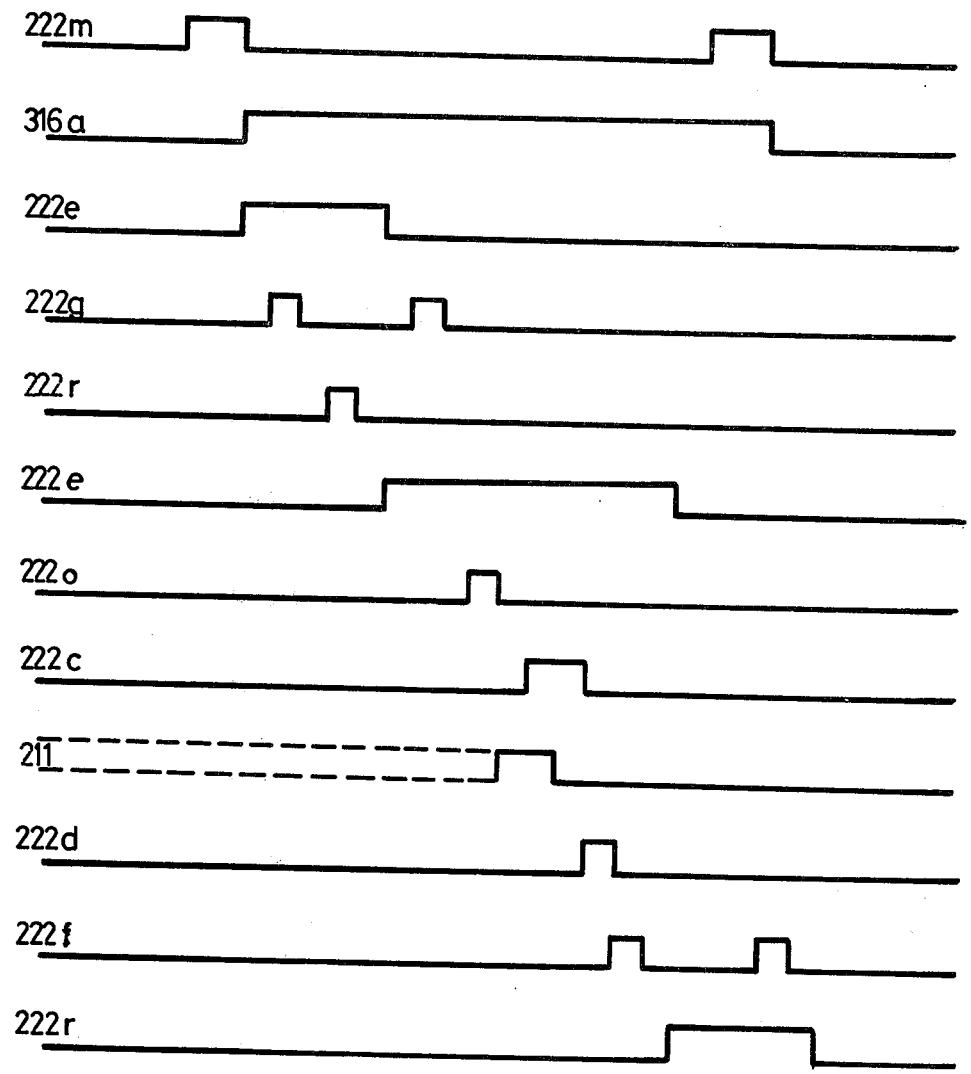

FIGS. 3, 4 and 5 show the shape of the pulse signals appearing at different points of the data processing unit, in order to facilitate the understanding of the working mode of the equipment.

It is shown in FIG. 1 that a rail 13 is fixed to the supporting block 1. Means for establishing the play of force and the elongation developing during the breaking process in the single filament yarns clamped within each of the measuring units are fixed to the said rail 13. It has already been mentioned that in this embodiment the said means are simple ones, viz. strain gauges. The sensor can be of a type supplying an output signal and the values of both the play of force and the elongation can immediately be derived therefrom. Likewise double sensors can be used, generating the electric signals which represent the force and the elongation separately. It is of no importance for the understanding and the reduction to practice of the invention which type of sensor is used; therefore, a single sensor is shown for each unit in the figure. The said sensors are considered as force transducers and in this sense do they appear in FIG. 2 when showing the data processing units more in particular. In FIG. 2 a special transducer is shown supplying the pulse train responsible for the value of the elongation. The sensor is thus hereinafter referred to as force transducer. The rail 13 in FIG. 1 is supporting for each measuring unit one of such sensors 14. The automatic clamping of the filament yarn is performed by the following components: the upper clamping head 12, the lower clamping head 15, the yarn-clamping jaws 22 /the clamping of the yarn samples 16 is shown in the FIG. 1, the nippers 18 catching the filament yarn, the latter being operated by bumper profiles 19, and the yarn feeding device 17 equipped with more arms. The loading of the yarn is performed by the preloading devices 20 and the yarn brake discs 21. A pair of chains 5 stretched by the chain pulleys 8 are used to produce the load, the chain pulleys 8 being wedged to the—parallelly arranged—upper and lower shafts 6 and 7. The pair of chains 5 drives the cross-rail 10 in vertical direction along the vertical guide paths 9. The tightness of the pair of chains 5 is maintained by the chain-tightening bearing support 11. The particulars as set forth above can be designed by those skilled in the art, using and multiplying the traditional one-channel tensile-strength testing machine or rather the necessary components of same, and even the working mode can partially be derived from that of traditional one-channel machines.

The driving gear of the embodiment described as example and realized with a worm gear 4 transmits the drive supplied by a program-controlled drive 24 comprising a main motor 2, a housing with a variable gear transmission 3 and a clutch 23, to the breaking mechanism.

The program-controlled drive 24 is controlled by means of a control electronics 300, according to a fixed program as follows:

Under the influence of starting, the cross-rail 10 is moved into its drafting position with full speed.

After the drafting of the yarn the cross-rail is moved down from its drafting position into the position corresponding to the set jamming length, with full speed.

After obtaining the position of the jamming length and closing of the yarn clamping jaw, the yarn-loading -driving operation is started with a speed according to the characteristics of the yarn sample. The sensors 14 supply information on the play of force proceeding during the operation into the data processing and control network. The data processing means evaluate the said information and, on the one hand, transmit them to the display and printing means and, on the other hand, send a signal to the control means. The breaking machine control electronics 300 transmits, accordingly, instructions to the program-controlled drive 24 as soon as the breaking process has come to its end; the said instructions cause the end of the cycle, the halting of the moving parts, the re-establishing of the initial state, and the preparations for the next cycle such as removing the filament yarn rests or clamping the new samples etc. The particulars of the mechanism of the breaking machine can in a known way be performed by those ordinarily skilled in the art excepting, of course, the means transmitting the control according to the invention and maintaining the interactive connection with the electronic system.

FIGS. 2a–2b show a block diagram of the data processing and main control network including mainly the main units participating in the data processing.

In the embodiment according to the example, in which n=10, further matching, shaping and converting units can be interposed on the direct coupling stages, but the existence of the basic couplings shown in FIGS. 2a and 2b is a basic condition of operation.

N sensors 14 were shown in FIG. 1. They appear in FIG. 2 as the first, second, third, . . . , n-th sensors 201, 202, 203, . . . , 210, and arranged at the breaking machine 200 consisting of n single breaking units. The data outputs of the said sensors 201 . . . 210 are connected each to one of the first, second, third, . . . , n-th comparators 211, 212, 213, . . . , 220 to the direct inputs of the latter. The outputs of the comparators 211 . . . 220 are coupled to a channel selector 221 at the output of which the data that were supplied by the breaking units as analog signals already appear in digital form.

A mutual data transfer takes place between the channel selector 221 and the control unit 222. The control unit 222 is coupled over an address channel 329, a read-in control channel, and a readout control channel to the RAM-memory 223 the data outputs of which are connected to a first and a second register 224 and 225. The data outputs of the said register 224 and 225 are connected to the inputs of an adder stage 226. The output of the adder stage 226 is connected to a D/A converter 227 the output of which is connected to the inverse inputs of the comparators 211 . . . 220.

The connections are generally symbolized by thin lines notwithstanding the fact that some of them may represent more than one channel; heavy lines are only used if the cumulative data flow is a characteristic feature of the connection path in question. The system is set forth in a manner leaving no doubt concerning the direction of data flow, and making it clear whether the path is all along a parallel one, or a multiple of elementary data is transferred parallelly, a single information is transferred, or the transfer of the information/group/ is performed in a manner such that a single path is connected to all channels and the signal is directed to only one of the said channels by addressing.

One output of the channel selector 221 is also connected to an input of the second register 225. The outputs of the AND-gates 301 . . . 310 are connected to the inputs of an OR-gate 312 with n inputs whereas the output of the said OR-gate 312 is connected to one input of a further AND-gate 315 with three inputs, and to the input b of the control unit 222. The output of the further AND-gate 315 is that one of the outputs of the channel selector 221 which is connected to one input of the second register 225. The channel selector 221 comprises a comparator logical network 313 /the design of which will be apparent to those ordinarily skilled in the art after knowing its function as set forth hereinafter/, and a multiplexing 4-bit counter 316 to each of the outputs of which is connected the other output of one of the AND-gates 301 . . . 310. The outputs of the comparators 211 . . . 220 are connected each to another input of the comparator logical network 313. Also, a control channel 331 performing mutual data transfer is provided between the comparator logical network 313 and the connecting point a of the control unit 222. One output c of the control unit 222 is connected to one input of the further AND-gate 315. One output m of the unit 222 is connected to the input of the 4-bit counter 316. One input of the further AND-gate 315 is connected to a pulse generator 314, designed in this case for a frequency of 0.1 MHz.

The signal transmitter/s/ supplying a pulse train representing the value of elongation is /are/ arranged at the breaking machine 200. Those skilled in the art —knowing the working conditions as set forth hereinafter —can design the said signal transmitter/s/ according to prior art for the different fields of application. In the shown embodiment it is an elongation pulse transmitter 311, coupled over its output to a 12-bit counter 318. The output signal of the said counter 318 shall also be coupled to a suitable input of the RAM-memory 223. Therefore a 12-bit line selector stage 319 is matched to the data inputs of the RAM-memory 223. The coupling of both the outputs of the counter 318 and the said output of the second register 225 to the respective inputs of the RAM-memory 223 takes place by supplying the output signals into the line selector stage 319, and the latter performs the coupling in due course.

The timing of the operations of the control unit 222 is controlled by the pulses of a clock 317 connected to one input of the control unit 222 and designed—in this embodiment—for 100 KHz. The information on the instantaneous states of the work of the breaking machine 200 is supplied by the breaking machine control electronics 300 over a path symbolized in FIG. 2a by two channels which are connected to the inputs h and i of the control unit 222. The FIG. 2a shows two further channels connected to the outputs j and k of the control unit 222. The said channels transmit the instructions concerning the future work of the breaking machine to the electronics 300.

Further parts of the data processing and control network are shown in FIG. 2b. The first and the second register 224 and 225 were shown in FIG. 2b as indispensable parts of the equipment. In this embodiment the first register 224 is a 12-bit buffer store whereas the second register 225 is a presetable 12-bit counter, and the RAM-memory 223 is besides connected over its output channel 328 also to other registers viz. to a first and second buffer store 321 and 322 serving to perform the control of the display and the printing means, respectively. The operating of the said buffer stores 321 and 322 is also controlled by the control unit 222 over a single line in FIG. 2b. A display means 323 is coupled to the first buffer store 321 such as a 4-numeral LED-display. The second buffer store 322 is over a channel performing mutual data transfer connected to a matching unit 324, and the said matching unit 324 is over another channel 332 performing mutual data transfer connected also to the control unit 222. Another channel 333 performing mutual data transfer serves to connect the said matching unit 324 to a data recording unit 327 more particularly to the input of a calculator 325 which is a part of the said data recording unit 327. The calculator 325 is connected over a data output channel 334 performing data transfer only in one direction to a printing unit 326. A level divider stage 320 is shown in both FIGS. 2a and 2b. In this embodiment this is a decimal divider /n = 10/. The data input of the said level divider stage 320 is connected to the output of the D/A converter 227 /see FIG. 2b/ whereas its data output is connected to the inverse inputs of the comparators 211 . . . 220 /see FIGS. 3a/. One output d of the control unit 222 is also connected to the level divider stage 320. One output u of the control unit 222 is connected to the control input of the line selector stage 319.

For the understanding of the operation of the described system it is necessary do scrutinize more particularly the character of the conversion at different levels mentioned already shortly hereinbefore.

The dc voltages supplied by the measuring bridges over their dc amplifiers can only be processed after converting them into digital signals. It has been mentioned that the solutions following the methods known in the prior art—be it the central A/D converter or the multiplication of known one-channel converters according to the number of parallel measuring units—are very sophisticated and extremely expensive. If using a central A/D converter and a digital multiplexer, the A/D converter must comply with very severe requirements. A resolving into at least 4095 different values-/i.e. 12 bits/ is required to obtain the necessary precision of the data processing. Assuming a standardized breaking time of 20 s, and approximating the breaking characteristic by a straight line, the growing speed of the output level of the sensors amounts to 1 bit/ms. This results is a mulplexing frequency of 2 KHz for n=10, i. e. the central A/D converter takes samples of any given channel with a periodicity of 5 ms. Supposing portions of the characteristic steeper than 1 bit/ms, it is expedient to diminish the period to 1 ms.

In this case the conversion time is restricted to not more than 100 $\mu$s. Supposing further that a complete conversion be performed in the last seconds of the breaking process /i.e. there are 4096 conversion steps/, the working frequency of the A/D converter is required to be not less than 40 MHz. For such a speed, high-speed circuitry is needed and difficulties arise. The solution according to the invention shows much more advantageous working conditions, especially speed data allowing the building of an equipment operating more reliably although equipped with very simple and, consequently, considerably cheaper components so that the whole equipment is much more economical and the investment for a multiplication necessary to perform a large-scale testing is within bearable limits. Hereinafter this is set forth in particular with reference to the embodiment as shown by way of example in the FIGS. 2a and 2b but the image obtainable by this description can be considered as generally valid.

The channel selector 221, the register 224, the register 225, the adder stage 226, the D/A converter 227 and the comparators 211 . . . 220 represent a n-channel A/D converter.

Considering one channel of said A/D converter, the result of the k-th conversion needs to be memorized in a certain section of the RAM-memory 223. Before proceeding—to the performance of the /k+1/-th conversion, the content of the section belonging to said channel shall be transferred into the presetable counter of the A/D converter. Thus, the A/D converter has only to process the level difference $\Delta$ U that took place between the two sampling instants. Supposing a slope of 1 bit/ms and a sampling frequency of 10 KHz as set forth hereinbefore, the converter has only to process a change of 1 bit between two sampling periods. 100 $\mu$s can be used for this operation so that our A/D converter can work at a 10 KHz frequency instead of the 40 MHz necessary according to prior art. It has been mentioned that the clock of the A/D converter has been chosen ten times quicker in order to increase the reliability.

The particulars of the whole working process will now be prescribed in five separate parts in order to facilitate the understanding:

1. 10 channel force sampling, storing of the samples, and conserving the peak values.
2. Automatic drift compensation.
3. Elongation sampling and storing.
4. Rupture control.
5. Data readout.

1. 10 channel force sampling, storing of the samples, and conserving the peak values.

Assume a condition in which the content of the 12 bit first register 224 is zero, the 12-bit first and second buffer stores 321 and 322 do still not take part in the data flow, the line selector stage 319 is connecting the outputs of the second register 225 to the inputs of the RAM-memory 223 and the comparator logical network 313 does also not work.

The outputs of the comparators 211 . . . 220 are at the logical H /high/ level, if the output levels of the sensors 201 . . . 210 exceed the output level of the D/A converter 227, and they are at the logical L /low/ level, if the output levels of the sensors 201 . . . 210 are lower than that of the D/A converter 227.

The output level of the OR-gate 312 with n inputs is either at the H or at the L level dependent on two conditions viz. which one of the comparators 211 . . . 220 is connected by the 4-bit counter 316 through the AND-gates 301 . . . 310 to the OR-gate 312 and what is the state of the selected comparator i.e. which logical state appears at its output.

If the control unit 222 couples a logical H level to its output c, and the OR-gate 312 is also in the H state, then the second register 225 accumulates the clock pulses received over its input and the incremental increase of its content is performed with a speed of 1 bit/$\mu$s. The second register 225 controls over the adder stage 226 the input of the D/A converter 227, thus, the output level of the latter is increasing—in this embodiment— with a speed of 2 mV/$\mu$s.

The sampling is performed in the following way:

Let us suppose that—when switching on the equipment—the states of the 4-bit counter 316, the second register 225, and the RAM-memory 223 are equally zero. The control unit 222 issues over its output m a pulse that shifts the counter 316 into its first position, i.e. a H level appears at its first output a. This state causes—over the addressing channel 329—the selection of a section of 12-bit length in the RAM-memory 223 for the first sensor 201, a so-called "force section". The control unit 222 issues at its output g a pulse into the readout control channel effecting the transfer of the content of the selected section of the RAM-memory 223 into the output channel 328. /It has earlier been stated that in this initial state the said content equals zero/. Then the control unit 22 issues a pulse to its output o that effects that the information supplied into the channel 328 is transferred into the second register 225. Then the output c of the control unit 222 is put into the logical state H i.e. the entry of the increments /clock pulses/ into the second register 225 is allowed. As a consequence of that, the output level of the D/A converter 227 is continuously increasing with a speed of 2 mV/$\mu$s until it reaches the output level of the first sensor 201 that is connected to the direct input of the first comparator 211. When the said two levels become equal, the output levels of the comparator 211, the first AND-gate 301, and the OR-gate 312 change from H to L, and the further incremental increase is inhibited.

The control unit 222 issues the L level to its output c /i.e. inhibits the further incremental increase of the content of the second register 225/, and issues a pulse to its output f causing the transfer of the content of the second register 225 over the data channel 335 into the selected section of the RAM-memory 223 from which the initial information had earlier been read out. Then the control unit 222 issues a shifting pulse to its output m by which the counter 316 is shifted into the next position. /Output c of the control unit 222 is at H level, output d at L level/.

The time diagram of the sequence as set forth hereinbefore is shown in FIG. 4. One under another, there are given the signals appearing at the following points of the network: 222m, 316a, 222e, g, o, c, 227 output, 221 output, 222.

The control unit 222 repeats the whole set of instructions with this difference that the address channel 329 is now selecting the memory section belonging to the second 202 sensor, etc. The /n+1/th shifting instruction of the control unit 222 effects that the counter 316 is again shifted into the first position.

When the control unit 222 issues over its output p a read-in instruction pulse, the second register 225 and the D/A converter 227, respectively, are loaded by the value of the first sample supplied by the sensor 201 since that value has been loaded into the RAM-memory 223 during the first sampling operation.

There are now two possibilities dependent on the output level of the sensor 201.

a. If the instantaneous output level of the sensor 201 does now not exceed the value that has been measured during the first sampling operation /it is lower or equal to the previous one/, the output of the first comparator 211 is in the L state, and consequently, the output of the OR-gate 312 and the input b of the control unit 222 are also in the L state. The control unit 222 allows in this case no incrementing and the content of the second register 225 gets re-loaded into the RAM-memory 223 without any change.

b. If, on the contrary, the instantaneous value of the output level of the first sensor 201 exceeds the value that has been measured during the first sampling operation, the outputs of the first comparator 211 and the OR-gate 312, and also the input b of the control unit 222 is in the H state. The control unit 222 issues over its output c the instruction "increment", and the second register 225 is shifted as many times as necessary to make up just the value of the change in level. In practice, the change will only be a single bit. When the content of the second register 225 is equal to the instantaneous value of the first sensor 201, the output of the comparator 201 changes again into the L state, and the control unit 222 causes the loading of the content of the second register 225 into the RAM-memory 223, i.e. the RAM-memory 223 will now store the new value as corrected by the incrementing. The signals appearing during this operation at different points of the circuitry are shown in FIG. 4; the symbols are the same as in FIG. 3.

The process is repeated step by step for all channels, the control unit 222 shifting in due course to the second, third, . . . , n-th channel and beginning than the next sampling cycle by shifting again to the first one.

2. Automatic drift compensation.

It is well-known that the draft of the measuring amplifiers causes an error in the output signal since there is a juxtaposition: an error component varying slowly dependent on temperature change, or power supply deviation is added to the signal. The output signal of the force measuring bridges used according to the invention is of the mV order, and the said error voltage is commensurate with it. The digitalization is performed with a resolution of more than 4000 steps—as mentioned above—so that the minimum increment is of the $\mu V$ order. It can be seen from the above that there is no way to perform a drift compensation immediately within the measuring bridge. The error includes also the contact potential of the connecting and soldering points and the drift of same as well as the instability error of the bridge caused, on the one hand, by the power supply deviation, and, on the other hand, by the instability of the strain gauges. It is obvious that the very frequent zero setting cannot be performed automatically in the bridge itself. Likewise impossible would be a manual zero setting considering the working rate of the n-channel equipment. The subsequent electronic drift compesation according to the invention is performed in the following way:

Previously to each breaking operation, at a time when the sensors are still under no load, the digital sampling and memorizing circuitry processes and stores the instantaneous zero errors of the single sensors. During the breaking operation—when the output signal of the single sensors consists of both the really measured value and the juxtaposed zero error of the given sensor—this output signal is corrected by the value of the zero error.

At the beginning of the breaking operation the breaking machine control electronics 300 issues over its first output a pulse to the input h of the control unit 222, the said pulse representing the instruction: "calibration", and the calibration begins. The output level of the sensors is equal to their zero error since there is still no load. The control unit 222 shifts—over its output m—the counter 316 into its first position, thus selecting the first comparator 211 belonging to the first sensor 201 and a section of 12-bit length in the RAM-memory 223, the so-called "error section" belonging to the first sensor 201. The unit 222 issues a blanking pulse at its output n which resets the second register 225, and another blanking pulse at its output p which resets the first register 224 whereas a logical H level at its output c allows the incrementing in the second register 225 over the further AND-gate 315. The second register 225 increases—through the adder stage 226—the output level of the D/A converter 227 until the said level becomes equal to that of the output of the sensor 201. The output of the comparator 211 changes then into the L state causing the same state—over the first AND-gate 301 and the OR-gate 312—at the input of the further AND-gate 315, and, thus the inhibition of further incrementing. The input b of the control unit 222 changes also to the L state and, thus, the unit 222 inhibits the incrementing over its output c, too.

The unit 222 issues over its output f a read-in instruction pulse; the content of the second register 225 is transferred into the error section of the RAM-memory 223 that belongs to the first sensor 201 over the data channel 335. The unit 222 now selects through the 4-bit counter 316 the second sensor 202, and designates— through the address channel 329— another error section in the RAM-memory 223 for the second sensor 202. Then the whole process is repeated for the second channel, etc. When the n-th channel undergoes the same process, the unit 222 puts an end to the working mode "calibration" and awaits—over its input i—the signal "measurement begins".

The breaking machine 200 threads the first yarn samples into the clamping heads and begins the stretching; at the same time the breaking machine control electronics 300 issues the "measurement begins" signal to the input i of the control unit 222, the working mode "measuring" begins. The unit 222 shifts the counter 316 into its first position and designates in the RAM-memory 223 over the address channel 329 the error section belonging to the first channel, then issues a "readout" instruction over its output g to the RAM-memory 223 that effects the transfer of the content of the error section into the data channel 328. A "read-in" instruction supplied by the unit 222 to its output r effects the transfer of the said information into the first register 224. The first register 224 is now loaded with the zero error established with the first sensor 201 during the "calibration" mode. The control unit 222 designates now—over the address channel 329—a force section for the first sensor 201, and issues a readout instruction to the RAM-memory 223 so that the content of the designated force section/according to our supposition the said content is still zero/becomes transferred into the data channel 328 whereas a read-in instruction appearing at the output o of the unit 222 effects the transfer of the channel information into the second register 225.

The contents of the first register 224 and the second register 225 are supplied into the adder stage 226 and the result of the addition to the input of the D/A converter 227. During the breaking operation the output level of any sensor is the following:

$$U_{xi} = U_{Ei} + U_{Hi}$$

where $U_{Ei}$ is the signal representing the real value of the sample bare of any zero error, $U_{Hi}$ is the instantaneous zero error of the given sensor.

The output level of the first sensor 201 is likewise:

$$U_{x201} = U_{E201} + U_{H201}$$

The input of the D/A converter 227 is over the adder stage 226 controlled by the algebraical sum of the content of the first and the second register, 224 and 225, resp. The first register 224 is only loaded with the zero error, the substracion of same means that the $U_{E201}$ value alone proceeds to the D/A converter 227 controlling the latter.

Then the control unit 222 issues a logical H to its output c and allows again the incrementing in the second register 225 over the further AND-gate 315. It can be seen from the above that the register becomes now loaded with the correct—correct zero error-free—value and this value will be stored in the force section of the RAM-memory 223. The same process is then repeated periodically so that—at the end of the breaking—any force section of the RAM-memory 223 will be loaded with the correct force value—bare of zero error—belonging to the given channel.

3. Elongation sampling and storing.

The electric signal representing the elongation of the yarn sample is supplied by a pulse generator in a manner such that a perforated disc runs in synchronization with the shaft of the driving motor of the stretching mechanism and a photo-electronic transducer is in this way supplied with a pulse train representing the angular displacement. The electric pulses appearing at the output of the said transducer are processed by a 12-bit counter. When sampling a certain channel, the control unit 222 effects the entry of the instantaneous content of the counter into the so-called elongation section of the RAM-memory 223.

The breaking machine control electronics 300 issues a pulse to the input i of the control unit 222, signalling the beginning of the elongation measurment. From then on a 12-bit counter 318 counts continuously the pulses appearing at the output of the elongation pulse transmitter 311. After having finished the sampling operation for a certain channel the control unit 222—having already effected the re-entry of the content of the second register 225 into the RAM-memory 223—designates over the address channel 329 the address of another section that shall receive the elongation value of the same channel. A logical H level issued over the output u of the control unit 222 effects the switching over of the line selector stage 319 so that now the data inputs of the RAM-memory 223 are connected to the output of the said counter 318. The control unit 222 now supplies over its output f a read-in pulse to the RAM-memory 223 and the content of the counter 318 enters the section designated over the address channel 329. The control unit 222 shifts the 4-bit counter 316 into the next position and effects over its output u the switching back of the lines selector stage 319 so that the output of the second register 225 is again coupled to the data input of the RAM-memory 223, and the train of instructions is periodically repeated.

4. Rupture control.

The device checks—during the breaking process after each sampling—whether the yarn sample underwent rupture or not. The rupture control is performed in the following way. The output level of the D/A converter 227 is divided by the level divider stage 320—the divisor is: n—and the diminished level is compared with the instant value of the given sensor. If the rupture has already taken place, the output level of the sensor falls practically to zero. The level at the output of the D/A converter 227 is always equal to the maximum level occuring during the previous cycles. If the voltage at the output of the tested sensor diminishes to e.g. a tenth of the maximum, the change of the comparator belonging to this sensor into the L state is inevitable. The comparator logical network 313 is sensing this state and a storing flip-flop which is a part of the network 313 gets into the H state as a consequence of which the access to the force and elongation sections belonging to the just tested channel becomes inhibited. After the rupture of the last filament yarn in a cycle, the comparator logical network 313 issues a "stop" signal to the control unit 222, the latter effecting the standstill of the breaking machine 200 and the data transfer towards the computer.

In the embodiment described by way of example, the control unit 222 designates the time when the comparators 211 . . . 220 shall be checked as for rupture over the control channel 331 coupled to the comparator logical network 313. The designation is controlled by the 4-bit counter 316 over the respective inputs of the logical network 313. The signals inhibiting the access to the sections in question and effecting the standstill of the machine are supplied to the control channel 331 by the comparator logical network 313. The level divider stage 320 is controlled over the output d of the unit 222. The signal shapes appearing during this working mode are shown in FIG. 5.

5. Data readout.

At the end of the breaking operation, i.e. when the last filament yarn undergoes rupture, the control unit 222 issues an instruction to the calculator 325 to begin the data acceptance. At the end of the breaking, the comparator logical network 313 signalizes over its output to the control unit 222 the end of the operation. The breaking machine control electronics 300 gets an instruction over the output k of the control unit 222 to stop the machine whereas the matching unit 324 gets its instruction over the output t signalling that the calculator 325 may begin the data processing. This instruction is sent to the calculator 325 over the programmable I/O channel 333, and the acknowledgement is sent back through the same control. Then the unit 324 asks the first force information over the data call channel 332 and the control unit 222. The control unit 222 designates over the address channel 329 the first force section, issues a readout instruction over its output g to the RAM-memory 223, and a read-in instruction over its a output that effects that the section information previously entered into the channel 328 is transferred into the first and second buffer stores 321 and 322. This information is then displayed as decimal quantity by the display means 323 /in this embodiment a LED-display/ that is coupled to the first buffer store 321. The control unit 222 issues now a pulse through the data call channel 332 to the matching unit 324 allowing the readout of the information from the second buffer store 322. The further data movement is now controlled by the calculator 325. When the 2×n data are taken over from the RAM-memory 223, the calculator 325 begins the data processing, and the results are supplied into the data readout channel 324. When the calculator 325 has finished its work, it signals the fact by a pulse sent over the matching unit 324 and the data call channel 332 to the control unit 222 allowing, thus, the beginning of the next breaking operation. The control unit 222 issues now a start instruction over its output j to the breaking machine control electronics 300, and the next period can being.

What we claim is:

1. In an equipment for the automatic, super-speed, and large-scale yarn-strength testing comprising a control unit for the concerted control of both the breaking process and the processing of the measured data, means for supplying electric signals proportional to the values of the breaking force and the elongation, respectively the said means being connected to at least one data processing unit(s) whereas the latter one(s) is (are) connected to a display and/or printing device, and the data processing unit(s) and the control unit are coupled to a computer the improvement in which n pieces (n being a positive integer) of breaking units each of them comprising at least one sensor (201 . . . 210) are mounted upon a common supporting block and coupled to a single, common, program-controlled drive (24) the program controlled inputs of which being connected to the outputs of the said control unit (222), and a data processing and control network is incorporated into the equipment comprising a RAM-memory (223) which is coupled over an address channel (329), a read-in control channel, and a readout control channel to the said control unit (222), and over its data output to the inputs of a first and a second register (224 and 225), the outputs of the said registers (224, 225) are coupled to the inputs of an adder stage (226), and the output of the second register (225) is also connected to the data input of the said RAM-memory (223), the output of the said adder stage (226) is connected to a D/A converter (227), and the output of the D/A converter (227) is connected to a set of comparators (211 . . . 220) over one of their data inputs whereas the other data inputs of the said comparators (211 . . . 220) are separately connected to one of the said sensors (201 . . . 210) each, and the outputs of the said comparators (211 . . . 220) are connected to the input of a channel selector (221) which is coupled with the said control unit (222) and the output of which is coupled to one of the inputs of the second register (225).

2. An equipment as claimed in claim 1, wherein the channel selector /221/ comprises n AND-gates /301 . . . 310/ connected to one of their inputs separately to one of the said comparators /211 . . . 220/ each, a counter /316/ being coupled over its outputs /a,b,c,/ to the other inputs of the said AND-gates /301 . . . 310/ and to its input to one output /m/ of the said control unit /222/, the outputs of the said AND-gates /301 . . . 310/ are connected to the inputs of an OR-gate /312/ with n inputs, the output of the said OR-gate /312/ is connected on the one hand to one input of a further AND-gate /315/ and on the other hand to one input /b/ of the said control unit/222/, the output of the further AND-gate /315/ is that output of the channel selector /221/ which is connected to the second register /225/, and the further AND-gate /315/ is connected over one of its inputs to a pulse generator /314/ and over another of its inputs to an output /c/ of the control unit, and the channel selector /221/ comprises a comparator logical network /313/ to the respective inputs of which are connected the comparators /211 . . . 220/ whereas the said network /313/ is also connected to the said control unit /222/ over a control channel /331/ performing mutual data transfer.

3. An equipment as claimed in claim 1 comprising a breaking machine control electronics /300/ which is connected over at least two channels to the respective inputs /h,i/, and over two channels to the respective outputs /j,k/ of the said control unit /222/.

4. An equipment as claimed in claim 1 comprising an elongation pulse generator /311/ the output of which is connected to the input of a counter /318/, and a line selector stage /319/ the outputs of which are connected to the data inputs of the said RAM-memory /223/ whereas its inputs are connected to the data outputs of the counter /318/ and second register /225/, respectively.

5. An equipment as claimed in claim 1 comprising a level divider stage /32/ to the input of which is connected the output of the said D/A-converter /227/ whereas its output is connected to one input of each comparator /211 . . . 220/.

6. An equipment as claimed in claim 1 comprising a display means /323/, and the data outputs of the said RAM-memory are also connected to the data inputs of the said display means /323/ over a buffer store /321/.

7. An equipment as claimed in claim 1 comprising a data recording unit /327/, and the data outputs of the said RAM-memory /223/ are also connected to the inputs of the said unit /327/ over a buffer store /322/ and a matching unit /324/.

8. An equipment as claimed in claim 7 wherein the data recording unit /327/ comprises a calculator /325/ and a printing unit /326/ and the calculator /325/ is connected over a channel /333/ performing mutual data transfer connected to the metching unit /324/ and over a readout channel /334/ performing only one-way data transfer to the printing unit /326/.

* * * * *